(12) United States Patent
Shoup et al.

(10) Patent No.: US 9,849,059 B2
(45) Date of Patent: Dec. 26, 2017

(54) HEADACHE MITIGATING APPARATUS

(71) Applicants: Andrew Shoup, Delray, FL (US); Travis Greenhalgh, Boca Raton, FL (US); Mike Angelini, El Sobrante, CA (US)

(72) Inventors: Andrew Shoup, Delray, FL (US); Travis Greenhalgh, Boca Raton, FL (US); Mike Angelini, El Sobrante, CA (US)

( * ) Notice: Subject to any disclaimer, the term of this patent is extended or adjusted under 35 U.S.C. 154(b) by 0 days.

(21) Appl. No.: 15/411,815

(22) Filed: Jan. 20, 2017

(65) Prior Publication Data
US 2017/0209333 A1 Jul. 27, 2017

Related U.S. Application Data

(60) Provisional application No. 62/281,196, filed on Jan. 21, 2016.

(51) Int. Cl.
A61F 5/08 (2006.01)
A61H 9/00 (2006.01)
(Continued)

(52) U.S. Cl.
CPC ............ *A61H 9/0078* (2013.01); *A61F 7/02* (2013.01); *A61M 21/02* (2013.01); *A61N 2/002* (2013.01); *A61F 2007/0002* (2013.01); *A61F 2007/023* (2013.01); *A61F 2007/0219* (2013.01); *A61F 2007/0228* (2013.01); *A61H 2201/0207* (2013.01); *A61H 2201/0214* (2013.01);
(Continued)

(58) Field of Classification Search
CPC .. A61F 7/00; A61F 7/02; A61F 7/0085; A61F 2007/0002; A61F 2007/0007; A61F 2007/0225; A61F 2007/0228; A61F 2007/023; A61F 2007/0231; A61F 2007/0233; A61F 2007/0234; A61F 2007/0268; A61F 2007/0269; A61F 2007/0273; A61F 2007/0054; A61F 2007/0056; A61F 2007/0059; A61F 2007/006

See application file for complete search history.

(56) References Cited

U.S. PATENT DOCUMENTS 7,051,379 B2 * 5/2006 Lambert .................. A42B 1/08
2/171

FOREIGN PATENT DOCUMENTS

CA 2436926 * 8/2003 ............... A61F 7/00

* cited by examiner

Primary Examiner — Robert Lynch
(74) Attorney, Agent, or Firm — Kajane McManus

(57) ABSTRACT

The headache mitigating apparatus includes at least a transverse strap configured to wrap around a user's head in the manner of a hat band and at least one strap configured to extend under the user's occipital bone and rest along the user's upper neck as well as extending over the head strap at a forward end thereof. The apparatus can include bladders in the transverse and occipital straps, respectively. The bladders can be filled simultaneously or separately with a pneumatic hand pump such as those found on sphygmomanometers or may include an inflation apparatus which is operable via a push button, in a manner similar to that in which self-inflating items inflate. At least one strap may also accommodate a gel pack for heating or cooling. One or both straps may include buckles or hook and loop closures configured to be adjusted to secure the apparatus to the user's head.

17 Claims, 12 Drawing Sheets

(51) Int. Cl.
*A61N 2/00* (2006.01)
*A61M 21/02* (2006.01)
*A61F 7/02* (2006.01)
*A61M 21/00* (2006.01)
*A61F 7/00* (2006.01)

(52) U.S. Cl.
CPC .. *A61H 2201/0257* (2013.01); *A61H 2201/10* (2013.01); *A61H 2201/102* (2013.01); *A61H 2201/1253* (2013.01); *A61H 2201/1604* (2013.01); *A61H 2201/165* (2013.01); *A61H 2201/1609* (2013.01); *A61H 2201/1685* (2013.01); *A61H 2201/5056* (2013.01); *A61H 2205/02* (2013.01); *A61M 2021/0016* (2013.01)

HEADACHE MITIGATING APPARATUS

CROSS REFERENCE TO RELATED APPLICATIONS

This application claims priority from provisional U.S. Application No. 62/281,196 filed on Jan. 21, 2016 and entitled Headache Mitigating Apparatus. The content of the above application is incorporated by reference in its entirety.

BACKGROUND OF THE INVENTION

The present invention is related to the development of a head gear device used in relieving headaches by applying pressure and/or temperature to specific areas of the upper neck/head area. Specifically, the suboccipital muscles which are known for causing headaches are targeted with therapeutic processes.

DESCRIPTION OF RELATED ART

In the United States alone, headaches affect millions of people every year. Depending on the person, headaches can be a mild or very severe pain. Almost everybody experiences headaches at some point in their lifetime. Some individuals even experience chronic headaches which can be debilitating. There are many types of headaches, each with a different sensation and cause. Some of the more common headaches are tension headaches, cluster headaches, sinus headaches, rebound headaches and migraine headaches. Each type of headache is caused by different factors so treating them may be difficult. There are numerous treatments for headaches ranging from medications, devices, preventative care, creams. Etc. It is proven that one type of treatment doesn't work for every headache. The most common treatment is often the use of drugs or medication but it's not for everyone. Many people choose to avoid this option due to potential side effects or complications with other medications. For this reason, better non-pharmaceutical methods of treating headaches are needed.

Cluster headaches typically affect men more than woman. They are recurring, typically around the eye and cause severe debilitating pain on a particular side of the head. Cluster headaches cause their victims to experience severe restlessness similar to a migraine. Other symptoms are that the eyes tend to water, and become photosensitive to light, causing an aversion to light. Sensitivity to noise, the nasal area tends to congest and swelling takes place around the eyes. Cluster headaches tend to recur form one attack every few days to eight per day. Cluster headaches tend to occur periodically, they can recur from one attack every couple of days, to eight attacks in a single day. The true cause is not yet known.

Another type of headache is the sinus headache. Common signs and symptoms include thick nasal mucous, and a clogged nose. These symptoms can be due to a viral infection, allergies, or air contamination. When the sinus becomes infected, pus can form in the sinus and lead to pain. Typically, sinus headaches are accompanied with fever. Sinus headaches can also cause middle ear problems. Headaches caused by sinus infections are usually treated with antibiotics. If the symptoms last less than ten days, it's typically caused by a virus but if the symptoms last more than ten days than it's considered bacterial. In this type of headache woman tend to be more affected than men.

Another type of headache is called the rebound headache. It is also referred to as the Medication Overuse Headache (MOH). Rebound headaches just as the name implies frequently occur daily, and can be painful. There cause can be attributed to the overuse of medications to relieve typical stress headaches, patients with this type of headache are best treated with preventive headache medications.

Migraine headaches are considered one of the worst headaches to get. They may have a genetic disposition; two thirds of people who get them tend to have cases running in their family. They tend to affect boys more than girls but after puberty the trend reverses where woman tend to have more cases. Migraines can last from two hours to several days, many times incapacitating the person. Light and noise sensitivity often occurs, accompanied with restlessness. The underline causes for migraines is not well known but a significant percentage of people can trace their migraines to dietary triggers.

Tension headaches are the most common type of headache. These headaches are very common because they're caused by stressors that are commonly found in everyday life. During tension headaches, people feel pressure around the head, temples, and/or back of the head and neck area. The level of pain may be mild to severe but they usually don't cause the patient to have nausea or vomiting. Although the pain is often mild, many people experience negative effects in their work, personal life and happiness due to tension headaches. Unlike most headaches, experts believe they know the cause of tension headaches. Stress, poor posture, lack of sleep and more causes tension to build up in the muscles of the back of the neck. More specifically, a group of muscles called the suboccipital muscles becomes tense.

The suboccipital muscles are a group of four muscles located below the occipital bone. The rectus capitis posterior major, rectus capitis posterior minor, oblique capitis superior, and the oblique capitis inferior form the suboccipital muscles. This group of muscles controls fundamental head movements, i.e., lateral flexion, rotation, and extension of the head. It is recognized that the suboccipital muscles are attached to the pain sensitive dura mater of the neck through a connective tissue bridge. This myodural bridge lies between the occipital bone and the 1st cervical vertebra of the spine and creates a connection between the rectus capitis posterior minor muscle and the dura mater. The dura mater is known to contain a vast collection of blood vessels and is innervated with meningeal branches from the trigeminal nerve. It has been proven that headache-like pain is produced by stimulation of these meningeal branches. It is known that people are subjected to many types of micro and macro trauma, which can be repetitive or non-repetitive. Injuries, imbalances or simple daily trauma such as poor posture, harmful sleeping positions, and stress are known to cause tension in the suboccipital muscles. As these muscles tighten, the myodural bridge pulls on the dura mater and elicits pain. This anomalous traction on the dura mater stimulates dural nociceptive fibers, resulting in painful, headache-like sensations.

It is believed that tension in the suboccipitals can cause multiple types of headaches including tension headaches, migraines, and cervicogenic headaches. It is known that migraine headaches generally produce a mild to severe throbbing pain that occurs unilaterally and may persist for hours or in rare cases, days. It is known that stimulating the trigeminovascular system, which is found in the dura mater, can cause migraine-like pain. Since the suboccipital muscles can transmit tension onto the dura mater through the dural bridge, it may be a possibility that they play a role in migraines. Cervicogenic headaches appear unilaterally, beginning in the back of the head and neck before progressing to the anterior portion of the head. These headaches are known to arise from cervical spine pain caused by dysfunction. The suboccipital muscles reach as far down as the second cervical vertebra, therefore contracted suboccipital muscles may produce a form of cervical dysfunction that can reduce the range of motion and function of the upper cervical spine and in turn cause headache pain.

Healthcare providers have used various methods to treat tense muscles of the neck in order to alleviate headaches. Some of the most common ways are to use massage, trigger point therapy, active release technique or spinal manipulation to loosen the suboccipital muscles and decrease tension. Other common methods to alleviate tension in the suboccipital muscles are cryotherapy, thermotherapy. It's known that during the first 24-48 hours after trauma the use of cold therapy will decrease blood flow to the targeted area and reduce pain and swelling. Applying cold temperatures to the suboccipital muscles are a reliable preventative action to reduce tension and prevent headaches. It is also known that the use of heat promotes vasodilatation causing diminished tension in the targeted muscles. Therefore, after the initial period of swelling occurs applying heat to the suboccipital muscles can relieve tension, thus reducing pain from headache. By decreasing the suboccipital muscle tension it may have effects on the nervous system, surrounding attachments to bones, capsules and ligaments. These effects may minimize the patient's pain depending on where the pain modulator is. Although decreasing tension in suboccipital muscles of the neck may not work for every type of headache, the use of cryotherapy or thermotherapy on the neck and/or head may help users cope with the pain from other forms of headaches.

It is the object of this invention to use the combination of adjustable pressure and/or temperature for therapeutic effects. In particular, the present invention relates to apparatuses intended to be secured on the head for relief of head pain. It is known that placing ice packs and tension around the neurocranium can significantly reduce pain. The uniqueness of this invention is that it uses self-adjusting pressure and/or temperature through the combination of gel packs, protrusions and/or air bladders to relieve tension in the suboccipital muscles of the upper neck and therefore relieving headaches. Studies have shown that when the suboccipital muscles are tense, they can cause headaches. This invention is unique and specializes by providing a pneumatic pressure and/or temperature simultaneously using an occipital strap directly on the suboccipital muscles.

SUMMARY OF THE INVENTION

According to the invention there is provided a headache mitigating apparatus comprising a first releasable and adjustable band which seats about the head in the manner of a hatband and a second adjustable band which hangs from the first band and at least seats engagingly around the muscular area below the rear skull just below the occipital bone for relieving tension in neck muscles, the bands including flexible and fillable bladders to accommodate filling with a desired material for use in headache mitigation.

It should be noted that the headache mitigating apparatus may include but is not limited to air type bubbles in its inner surface for providing comfort to the user as pressure is applied.

In another embodiment not shown protrusions on the hatband strap, and/or occipital strap may be used to apply direct pressure to specific areas of the head or pressure points. These protrusions may be a variety of different shapes, including but not limited to, circular, oval, triangular, square, rectangular, pyramidal, or hexagonal and may be made of any material.

In another embodiment not shown, the inside of the head strap, and/or the suboccipital strap may include a padding to make the inner surface more comfortable for the user. The padding may be but is not limited to a foam material such as polyurethane foam, memory foam or high density foam.

In another embodiment not shown the hatband may incorporate, but is not limited to, various patterns to allow the hatband to apply pressure on certain parts of the head for better securing and comfort. The headache band may produce circumferential pressure or pressures on specific areas of the head.

In another embodiment not shown a sticky fabric may be used to better grip the skin and hold the headband in place.

In another embodiment not shown an attachable strap may be situated around the user's jaw to help relieve TMJ (Temporomandibular Joint Disorders).

In another embodiment not shown, and not limited to, another strap may be used that goes over the top of the user's head to better secure the device. This strap may be permanently sewn to the headband strap or removably coupled via buckles, hook and loop fasteners, etc.

In another embodiment not shown the headband device may have but is not limited to various slits throughout for inserting various sized gel packs including the hatband strap.

Another embodiment not shown incorporates, but is not limited to, magnets that can be placed inside the carious slits throughout the headband device.

In another embodiment not shown the headband device may incorporate in combination with or by itself aromatherapy scents into the slits of the headband.

In another embodiment not shown the headband device may incorporate but is not limited to one or more manual or automatic air pumping devices connected for inflating the headband including a manual/automatic pump system incorporated as a means of inflating and deflating. In certain embodiments, the air pumping device may be removably attached for the users ease of use.

In another embodiment not shown, the bladders are not present. Pressure to the targeted area is applied by the suboccipital strap by manual means.

It should be noted that the pump, air valve or any system used for inflation of the bladders may be incorporated anywhere on the head mitigation apparatus.

In another embodiment, the area of each bladder(s) and the force of air delivered by the pump into said bladder(s) may create a $P_h$ of at least 0.01 lb$_f$/in$^2$ in each bladder whereas $P_h = F_a/A_b$. ($P_h$=Pressure in headband bladders, $F_a$=force applied by pump to an individual bladder, and $A_b$=the area of an individual bladder).

In another embodiment, when the headband is situated on the user's head/neck, the summative $P_h$ from the bladder(s) creates a $F_h$ greater than 0.1 kg·m/s$^2$ to the user's head/neck whereas $P_h$=Pressure in bladders, $F_h$=Force applied to the head, $F_a$=force applied by pump to an individual bladder, $A_b$=the area of an individual bladder and $P_h = F_a/A_b$.

BRIEF DESCRIPTION OF THE DRAWINGS

The invention will be more readily understood after reading the following detailed description of the preferred embodiment of the invention in combination with the drawings in which.

DESCRIPTION OF THE PREFERRED EMBODIMENTS

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 3:
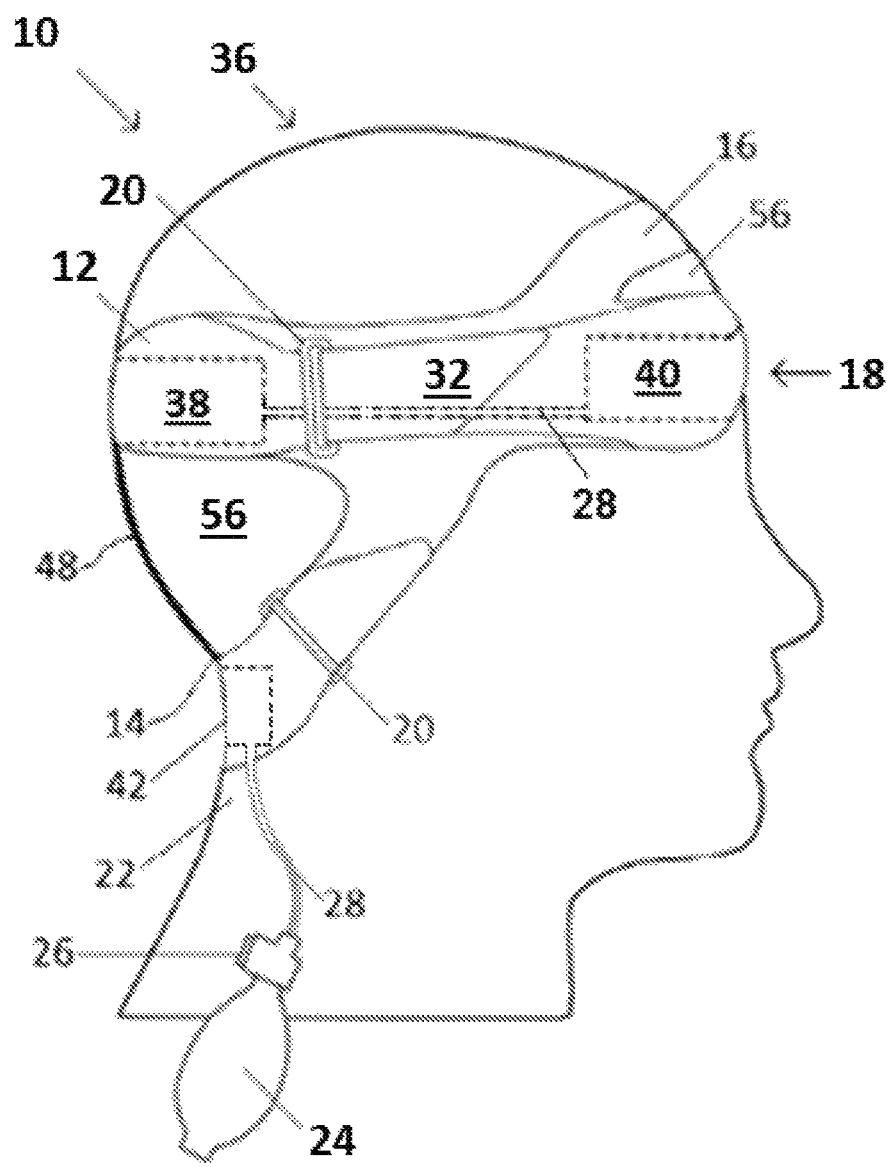

A first embodiment of the present invention will be described next with reference to FIG. 1 of the drawings. This embodiment comprises a headache mitigating apparatus (10) consisting of a head strap (12) that completely circles the circumferences of the user head (36). A suboccipital strap (14) is used in connection with the head strap (12), not limited to, but in union with the suboccipital middle connector member (48). The suboccipital middle connector member (48) helps provide stability of the device by connecting itself to the head strap (12). Its purpose is not limited to but includes supporting the head mitigating apparatus (10) to the head (36 of FIG. 3). Gaps (56) are located just below the front upper strap (16) and on opposite sides of the suboccipital middle connector member (48). Its purpose is to lighten the headache mitigating apparatus and to provide air circulation to certain areas of the head (36). In addition, a front head strap bladder (38) is used to apply pressure to the back side of the head alleviating certain types of headaches Suboccipital bladder (42) is used to apply pressure to the suboccipital muscles which are the main cause of many headaches. Another bladder (40) shown in FIG. 3 is used to provide pressure to the forehead. An Inflation bulb (24) generates air pressure to the bladders by a squeezing action that introduces air through a tube (28) directed to the individual bladders simultaneously and uniformly in nature. Bladders (38,40, 42) are all connected through internal tubing (not shown) that may take different passages inside the head mitigating apparatus (10). Strap buckles (20) are located uniformly to the sides of the suboccipital strap (14) and are used to adjust the head mitigating apparatus (10) to the individual user's head (36 of FIG. 3).

Figure 1:
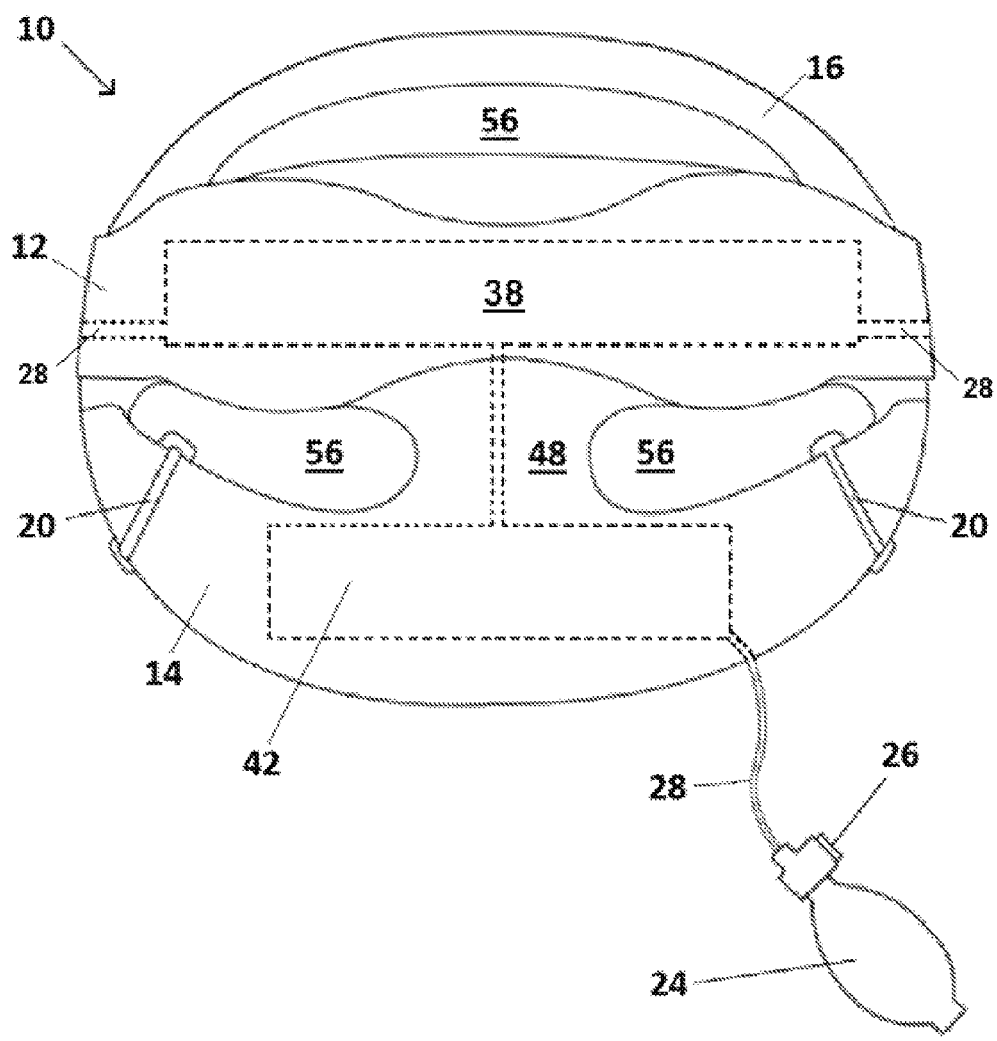
FIG. 1 provides a rear perspective view of a first embodiment of the headache mitigation apparatus of the present invention.
Figure 2:
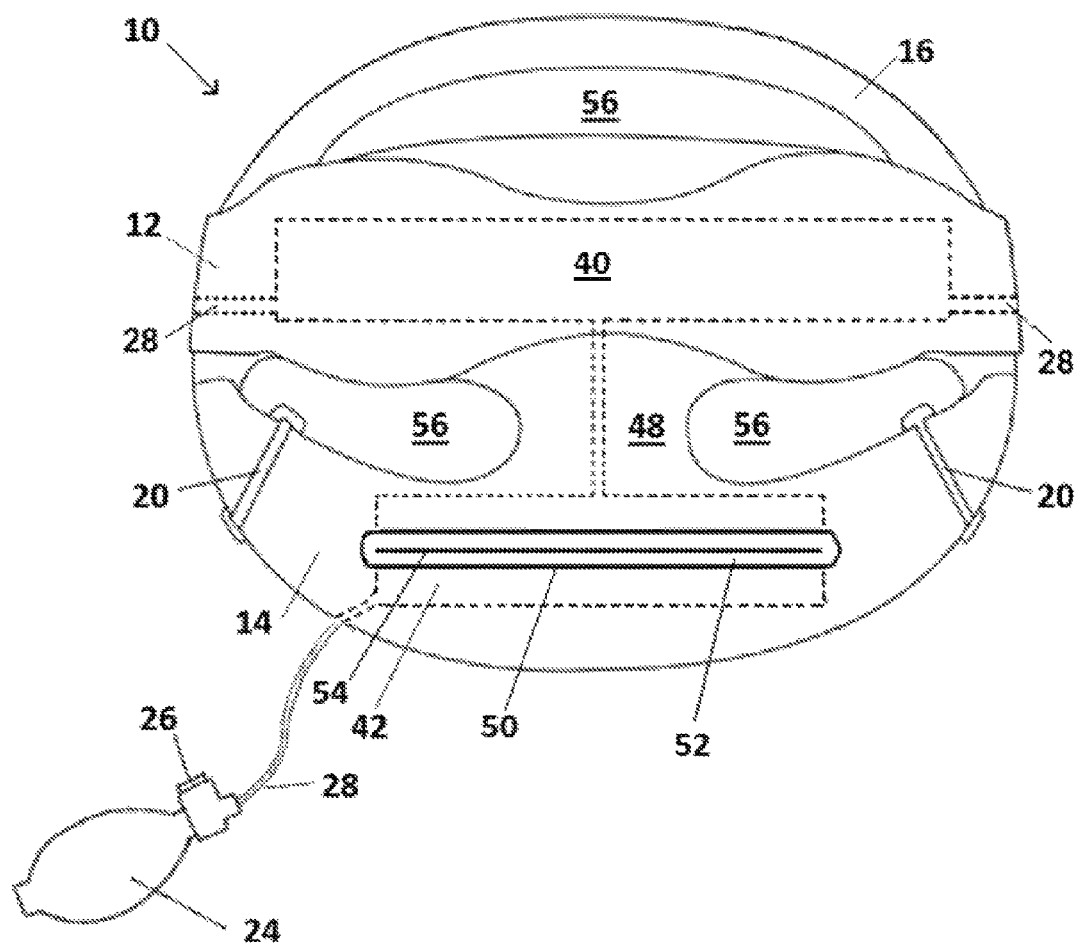
FIG. 2 provides a front perspective view of a first embodiment of the headache mitigation apparatus of the present invention FIG. 3 provides a side perspective view of the apparatus of FIG. 1 situated on a user's head.

In FIG. 2, a front perspective view of the apparatus of FIG. 1 is illustrated. This embodiment comprises a headache mitigating apparatus (10). Consisting of a head strap (12) that completely circles the circumference of the user head (36). A suboccipital strap (14) is used in connection with the head strap (12), not limited to, but in union with the suboccipital middle connector member (48). In this view, bladders (38,40,42) are not depicted to better demonstrate the suboccipital pocket (50) which may be used to insert a cooling gel pad or warming pad (not shown). The cooling/warming pad may be inserted through slit (54) or an suboccipital insertion/removal bladder may be used. In alternative embodiments, the pocket (50) may also house different types of inserts including but not limited to protrusions, aroma therapy inserts and magnets. In other alternative embodiments, there may be one or more slits placed in various positions on the headband such as but not limited to anywhere on the suboccipital strap (14) or head strap (12).

With respect to FIG. 3, a side perspective view of the preferred embodiment is illustrated showing the head strap (12) securely attached around the circumference of the head (36). The headache mitigating apparatus (10) snuggly fits around the front forehead (18) and suboccipital (14) strap by means of strap buckles (20) Adjustment of the straps (12, 14,16) are used to comfortably secure the head mitigating apparatus (10) to different head (36) sizes. Bladders (38,40, 42) are all inter connected with tubing (not shown) that permits even air pressure throughout. Inflation bulb (24) provides a means of manually applying air pressure through tube (28) to the suboccipital bladder (42), head rear bladder (38), and forehead head strap bladder (40). Gap areas (56) permit air circulation to those parts of the head and make the head mitigating apparatus light. The suboccipital middle connector member (48) helps provide stability of the device by connecting the suboccipital strap (14) to the head strap (12). Pressure is applied to the forehead area (18) by forehead bladder (40). The suboccipital strap (14) is typically positioned just above the upper neck area (22), below the suboccipital bone (not shown). Its main purpose it to provide pressure to the suboccipital muscles. When the user wishes to reduce pressure from the bladders (38, 40, 42) the pressure release valve (26) is used. It should be noted that the invention is not limited to but may use a bladder type cuff device for pressurizing the bladders (38, 40, 42). A lower occipital strap end (30) is used to pull the suboccipital strap (14) comfortably to the upper neck area (22). An upper head strap end (32) is used to fasten the head strap (12) comfortably around the user, and also used to loosen the head mitigating apparatus.

Figure 4:
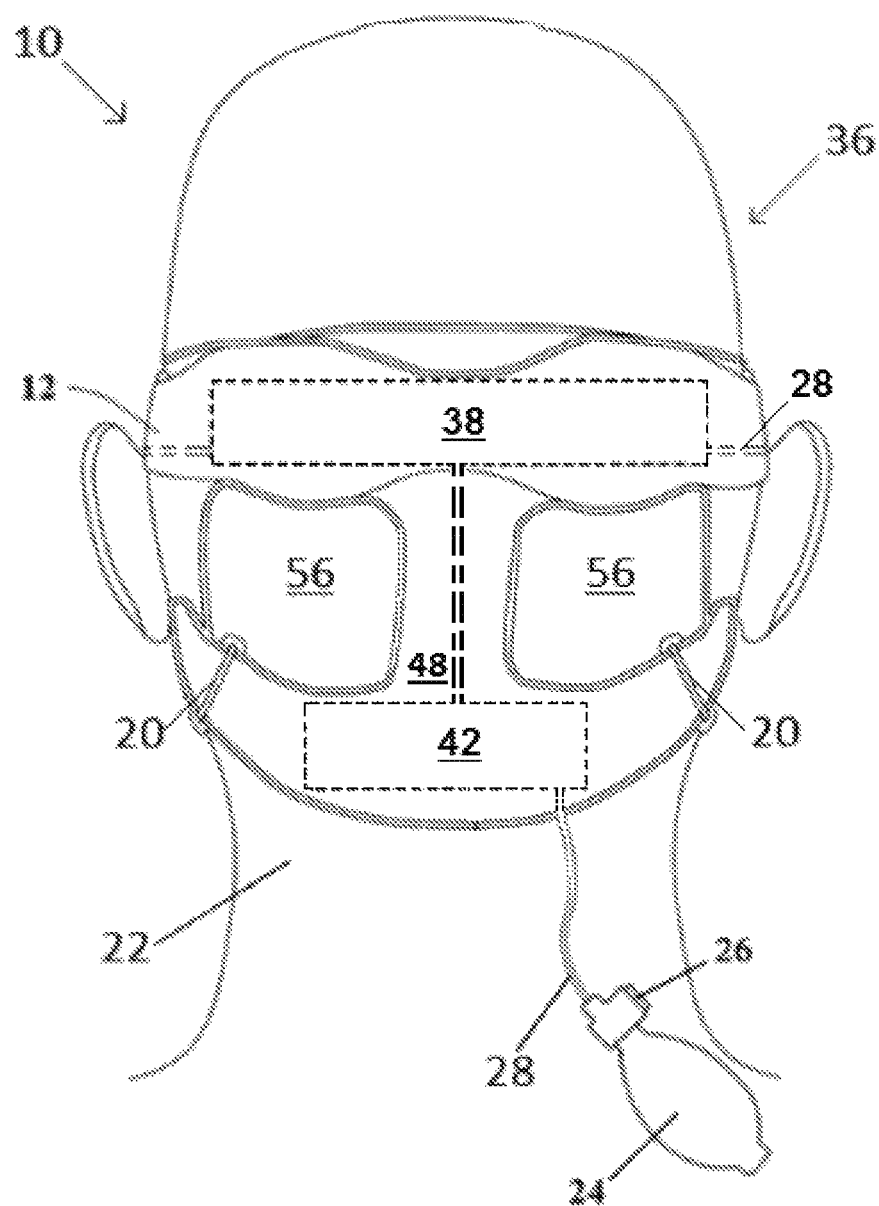
FIG. 4 provides a rear perspective view of the apparatus of FIG. 1 situated on a user's head.

With respect to FIG. 4, a back-head perspective view of the preferred embodiment is illustrated clearly showing how the head strap bladder (38) and suboccipital bladder (42) apply pressure to the back side of the head. Suboccipital middle connector member (48), clearly connects the head strap (12) section to the suboccipital strap (14). Gaps (56) are clearly shown providing ventilation to the rest of the head (36). Straps (20) can be easily adjusted by the user for each side. The upper neck area is located just below the suboccipital strap (14) where the sub occipital muscles are located. The inflation bulb (24), pressure release valve (26) and tube (28) can be moved to the side after use freeing up the user to move around. In some embodiments, the inflation bulb (24) may be detached from headache mitigating apparatus (10).

Figure 5:
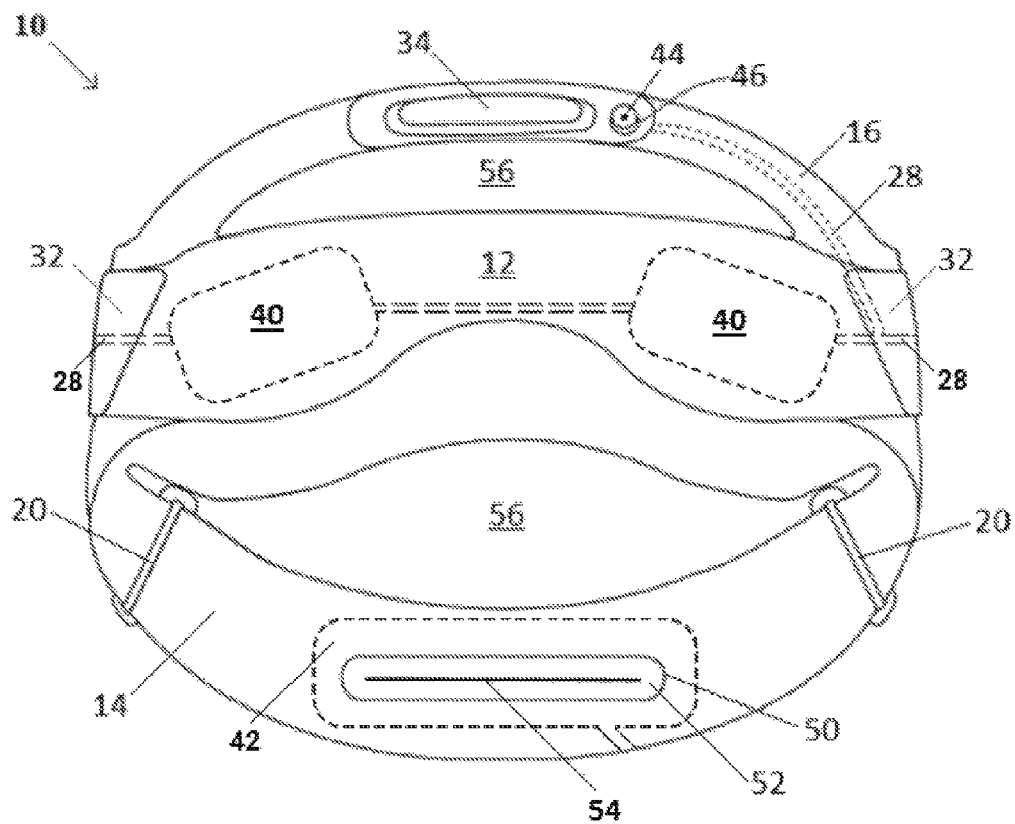
FIG. 5 provides a front perspective view of another embodiment of the headache mitigation apparatus of the present invention.

With respect to FIG. 5, a slightly different embodiment is used whereby the suboccipital middle connector member (48) is not incorporated, and an integral hand pump (34) is used at the front upper strap (16). When hand pump (34) is actuated, air is pushed through tube (28) to the internal bladders (not shown) of the headache mitigating apparatus (10). Straps (20) are used to adjust the suboccipital strap (14) to a comfortable fit for the user. Upper head strap ends (32) are used to fasten and adjust the head strap (12). Since no suboccipital middle connector member (48) is used a wider gap area (56) is created. This helps provide more ventilation and cooling for the user. This type of design helps provide a slightly different pressure to the suboccipital muscles. When it is desired to unpressurize the hidden bladders (not shown), air release button (46) is held so air may be released. In addition, in this alternative embodiment a suboccipital pocket (50) may be used to insert a cooling gel pad or warming pad (not shown). The cooling/warming pad may be inserted through slit (54) or an suboccipital insertion/removal bladder may be used.

Figure 6:
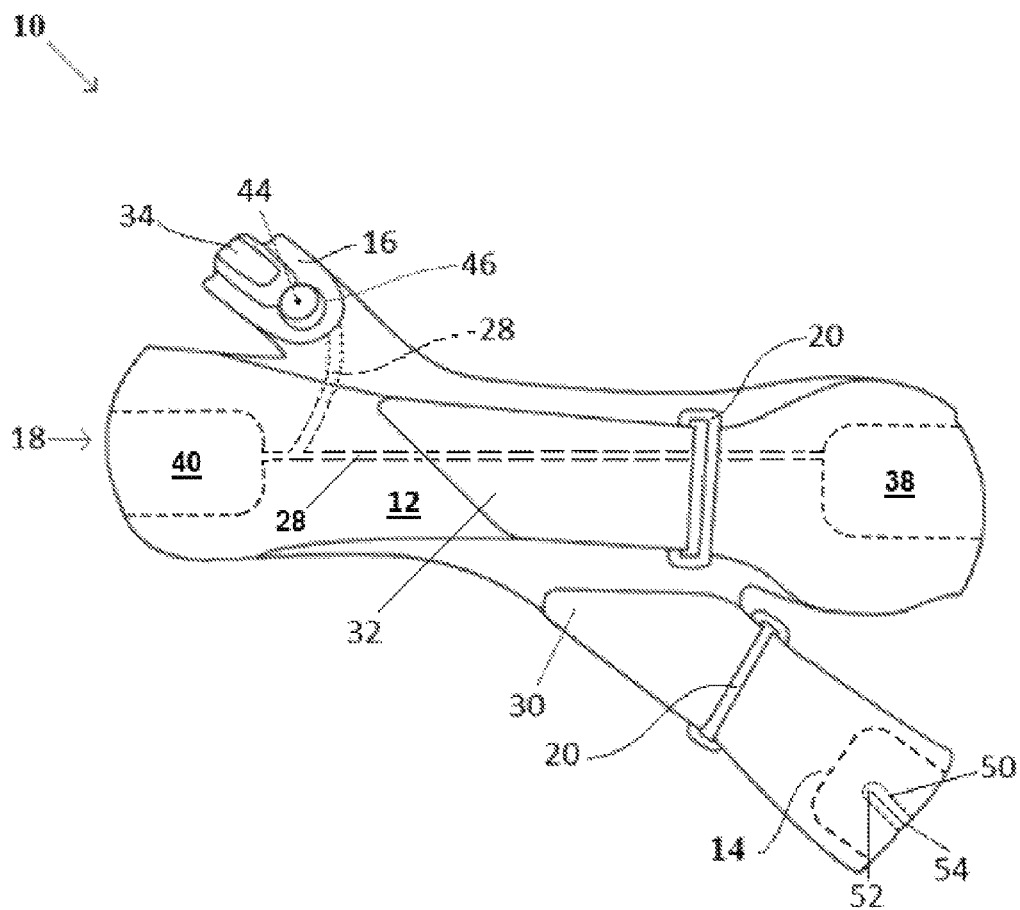
FIG. 6 provides a side perspective view of the apparatus of FIG. 4.

With respect to FIG. 6 a side perspective view of the alternative head mitigating apparatus (10) is illustrated clearly showing how the upper head strap end (32) is used to fasten and adjust head strap (12). Air pressure can be inserted into the bladders by hand pump (34) connected to a tube (28) going to different bladders (not shown). Lower suboccipital strap end (30) is also used to adjust the fit of the occipital strap to the back-neck area. Suboccipital pocket (50) can hold a heating/cooling gel to stimulate the occipital muscles when pressure is applied to the bladders (not shown). The gel is inserted through the suboccipital slit (54). This design does not use a (suboccipital middle connector member (48).

Figure 7:
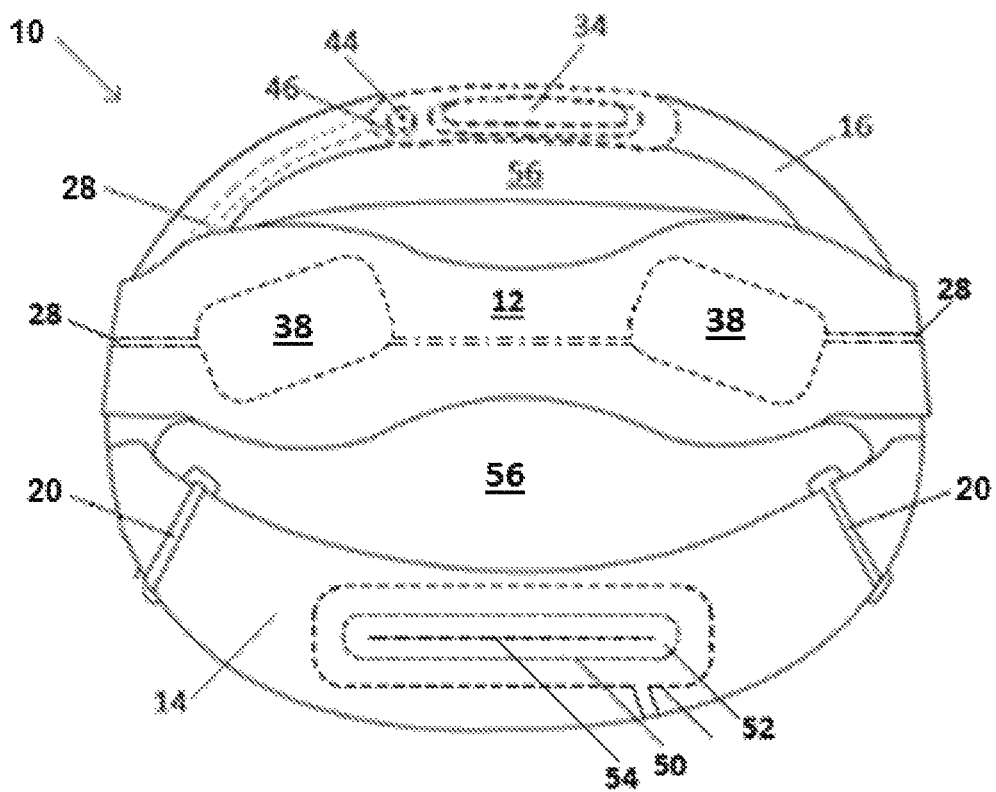
FIG. 7 provides a rear perspective view of the apparatus of FIG. 4.

With respect to FIG. 7, a rear perspective view of the alternative head mitigating apparatus (10) is illustrated incorporating all the same features as that of FIG. 6.

Figure 8:
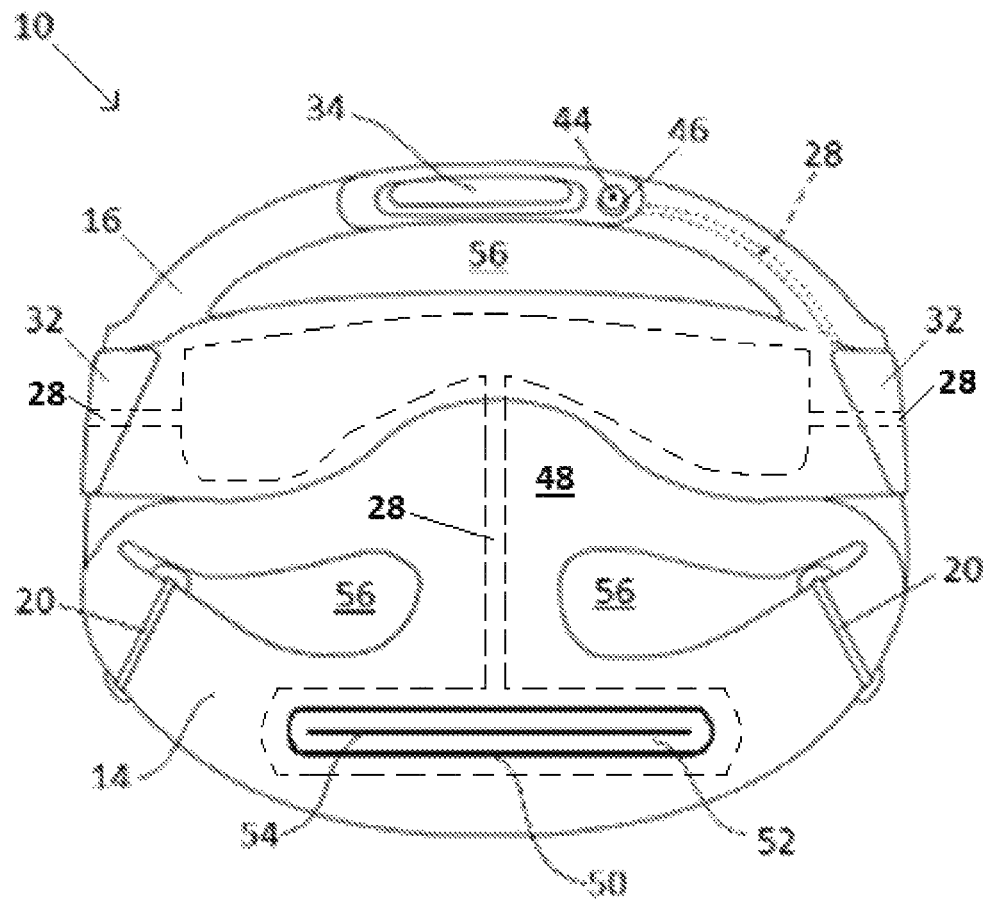
FIG. 8 provides a front perspective view of another embodiment of the headache mitigation apparatus of the present invention.
Figure 9:
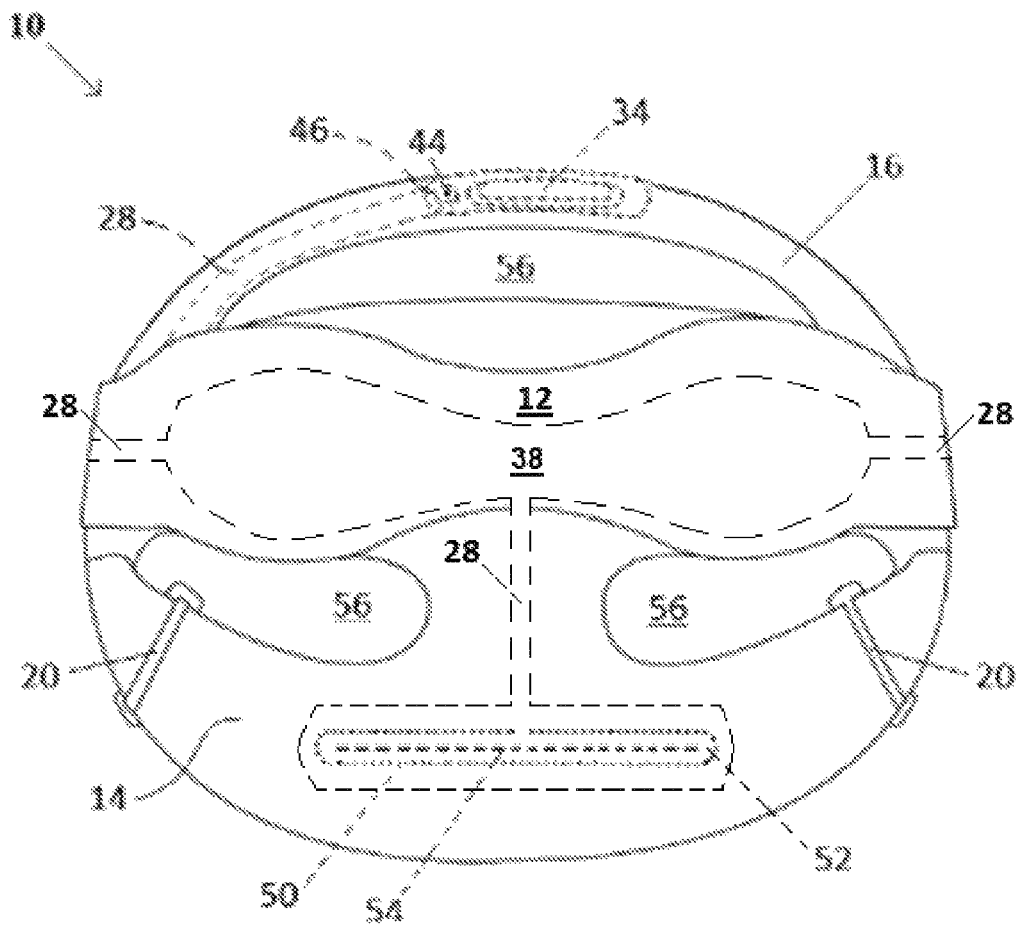
FIG. 9 provides a rear perspective view of the apparatus of FIG. 7.
Figure 10:
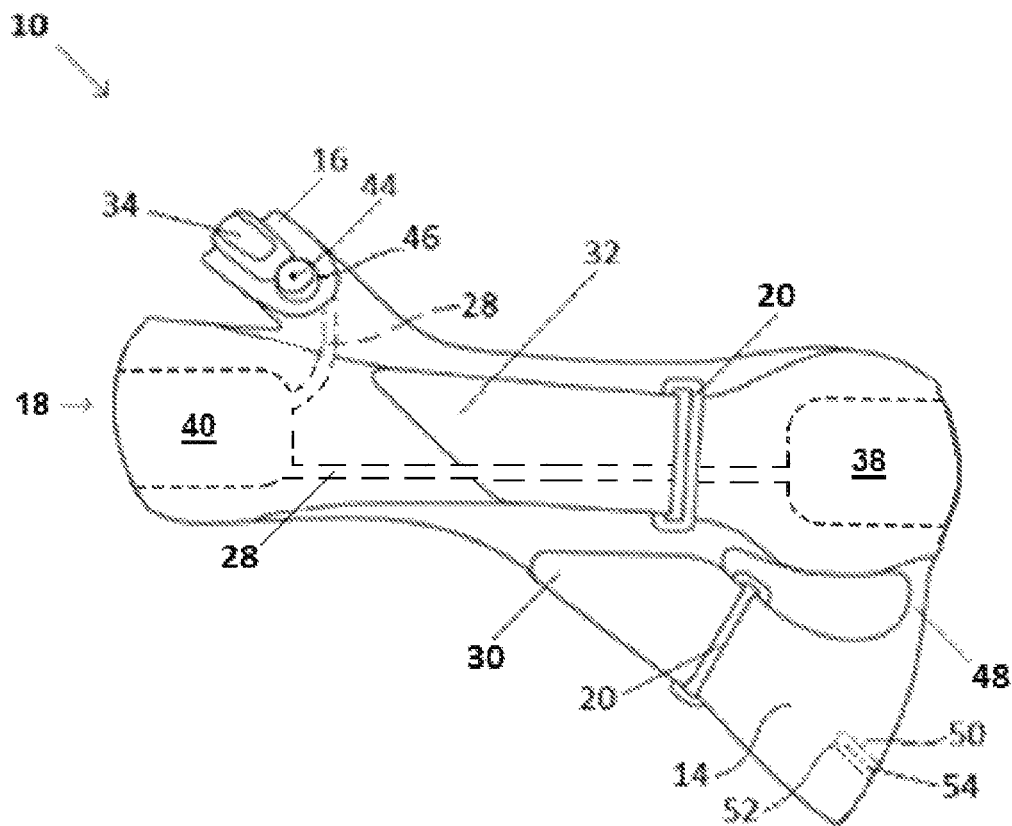
FIG. 10 provides a side perspective view of the apparatus of FIG. 7.

With respect to FIG. 8, a front perspective view of an alternative embodiment of the head mitigating apparatus (10) incorporating the suboccipital middle connector member (48) and using a hand pump (34) for inflation is illustrated. Gaps (56) are used to provide air circulation to the user. Suboccipital middle connector member (48) is used to provide a path to the head strap (12), Strap buckles (20) are used to securely fasten the suboccipital strap (14) to the upper neck area (22). Two upper head strap ends (32) are used to pull, fasten and adjust head strap (12) to the user. FIGS. 5, 6, 7 are similar in nature to FIGS. 8, 9, 10 with the exception of the suboccipital middle connector member.

Figure 11:
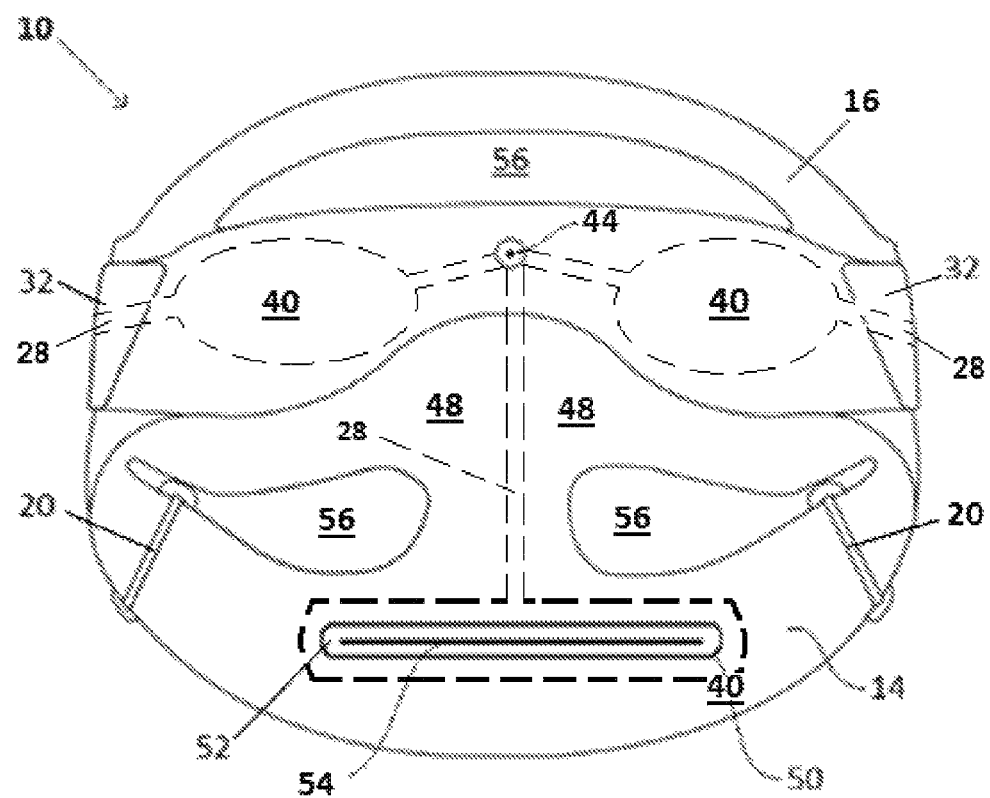
FIG. 11 provides a front view of an alternative embodiment of the head mitigating apparatus with an inflatable air valve.

With respect to FIG. 11 a front view of an alternative embodiment of the head mitigating apparatus with an inflatable air valve (44) is illustrated. In this embodiment, the user can inflate the internal bladders (not shown) by inserting an air pin into air valve (44). The same air valve (44) is used to deflate pressure to the internal bladders. Again, in this embodiment the forehead bladder (40), head strap bladder (38) and suboccipital bladder (42) are not shown but are all connected internally by a tube (28) configuration applying equal pressure throughout.

Figure 12:
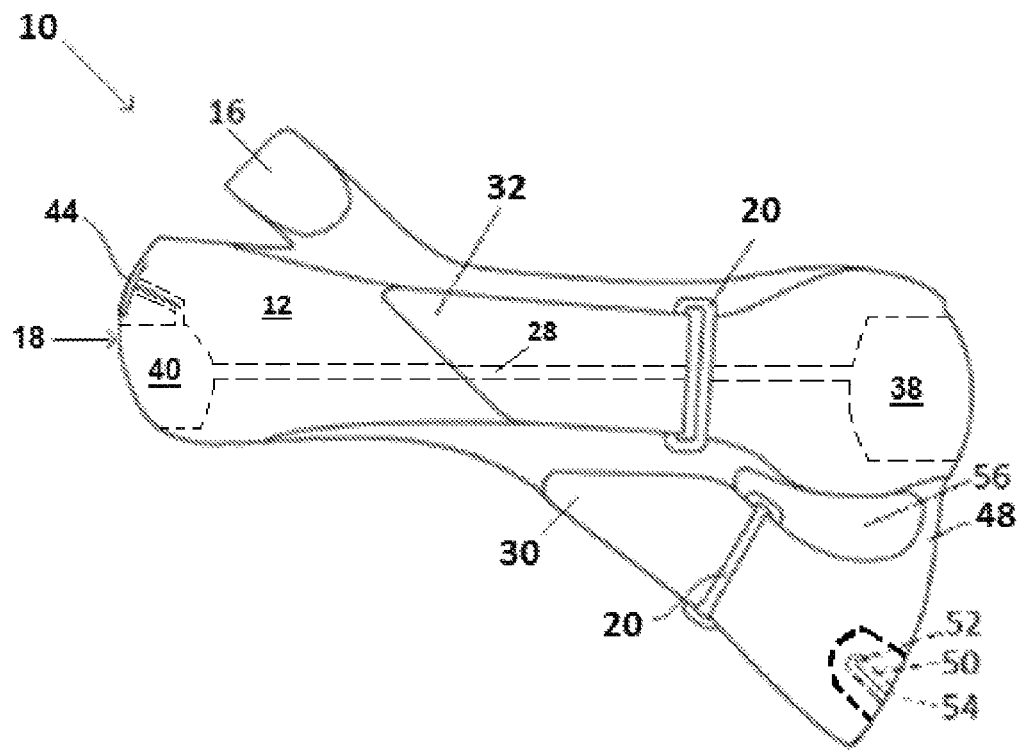
FIG. 12 provides a side perspective view of an alternative embodiment of the head mitigating apparatus with an inflatable air valve.

With respect to FIG. 12 a side perspective view of an alternative embodiment of the head mitigating apparatus (10) with an inflatable air valve is depicted. Inflatable air valve (44) is located at the forehead area (18) of the user. Head strap area (12) has internal bladders located in the front and rear used to apply pressure to the head and to the sub occipital bladder (42) not shown in this illustration. The suboccipital strap (14) and head strap (12) use strap buckles (20) for making adjustments to the head and neck area. A suboccipital pocket (50) is also used whereby a cooling gel or heating pad can be inserted through the suboccipital slit (54) and rest in pocket (50).

It should be noted that the headache mitigating apparatus may be configured but not limited to industry standard materials often used for head use. The bladders may be filled in synchronicity or independently from each other with air for pressurization, which may be either identical or different, in the manner in which a blood pressure cuff is inflated. Each user can distribute pressure discriminatingly to determine what works best for their particular type of headache. Also, the strap that wraps around the upper neck region 15 may hold accessory Insertable/removable bladder(s) (52) of material such as gel that can be heated or cooled which is inserted into a central area of the occipital strap (14) via a slit (54) leading into a small pocket (50) provided therein, which are only described here once, for brevity It should be noted that the invention is not limited strap buckles (20) such as those illustrated, but may use other suitable connectors, not limited to but including hook and loop structures, ratcheting mechanisms, etc.

Loosening contraction of the muscles in the upper neck area (22) ultimately decreases tension on structures attached thereto, as known in the art, which causes headache pain. It should be noted that the pump device (34) is similar in nature as other industry standard devices that allow air to be drawn and or released When the bladders are inflated, the pump may apply a constant or pulsed pressure to help loosen tightly contracted muscles in the upper neck area (22). Loosening contraction of the muscles in the upper neck area (22) ultimately decreases tension on structures attached thereto, as known in the art, which cause the headache pain. It should be noted that the pump device is similar in nature as other industry standard devices that allow air to be drawn and or released.

The interior bladders (18, 38, 42) may be, but is not limited to, being filled simultaneously or separately, to apply specific pressure to a desired area. The bladders are expanded manually or mechanically by means of a pump.

The headache mitigating apparatus (10) according to the present disclosure alleviates numerous types of headaches using inflatable bladders to relieve upper neck area (known as suboccipital) muscle tension. The apparatus (10) in its various embodiments comprises a head strap (12) that wraps around the head in the manner of a hatband and at least one other strap, a suboccipital strap (14) that passes under the occipital bone (not shown) resting along the upper neck area (22) as well as extending over and above a forward area (18) of the head strap (12), creating a narrow X shape to the headache mitigating apparatus (10) when viewed from the side. Both straps (12, 16) are primarily configured with bladders (38, 40, 42). Both straps 12, 14 are adjustable to fit the user's head and may be attached and held in position by suitable buckles 22 such as those illustrated, or with other suitable connectors, not limited to but including hook and loop structures, ratcheting mechanisms, etc.

A headache mitigating apparatus comprising at least a first adjustable strap which snugly engages about the head of a wearer about a front to back circumference of the head and at least a second adjustable strap extending downwardly and rearwardly from opposite positions along the first adjustable strap into a position where it abuts an area at the juncture of the head and an area the neck known as the suboccipital area, with at least the second adjustable strap being releasably inflatable to apply pressure against the suboccipital area.

A headache mitigating apparatus of claim 1 wherein the first adjustable strap is also releasably inflatable.

The headache mitigating apparatus of claim 1 wherein the second adjustable strap further incorporates a forwardly and upwardly adjustable extension which extends across a forehead portion of the head of the wearer.

The headache mitigating apparatus of claim 3 wherein the forwardly and upwardly adjustable extension which extends across a forehead portion of the head of the wearer is also releasably inflatable.

A headache mitigating apparatus wherein the accessory further wide adjustable strap positioned across a crown of the head of the wearer is also releasably inflatable.

A headache mitigating apparatus wherein the straps include bladders therein which may be inflated or deflated via use of a hand pump.

A headache mitigating apparatus wherein the straps include bladders therein which may be inflated or deflated via use of a mechanical pump carried by the apparatus.

A headache mitigating apparatus wherein the straps further include cavities therein into which replaceable hot or cold inserts may be inserted to apply heat or cold as desired.

A headache mitigating apparatus wherein the straps further include hot or cold inserts which are permanently affixed to the straps.

A headache mitigating apparatus further including a pressure control valve to limit inflation of the bladders.

A head mitigating apparatus, wherein all inflatable bladders are interconnected.

A head mitigating apparatus wherein the area of each bladder(s) and the force of air delivered by the pump into said bladder(s) may create a $P_h$ of at least 0.01 lb$_f$/in$^2$ in each bladder whereas $P_h=F_a/A_b$.

A head mitigating apparatus, wherein the summative $P_h$ from the bladder(s) creates a $F_h$ greater than 0.1 kg·m/s$^2$ to the user's head/neck whereas $P_h$=Pressure in bladders, $F_h$=Force applied to the head, $F_a$=force applied by pump to an individual bladder, $A_b$=the area of an individual bladder and $P_h=F_a/A_b$.

The headache mitigating apparatus of claim 9 wherein the cavities may alternatively house protrusion inserts that apply localized pressure.

The headache mitigating apparatus of claim 9 wherein the cavities may alternatively house magnets.

The headache mitigating apparatus of claim 9 wherein the cavities may alternatively house aromatherapy inserts.

A headache mitigating apparatus comprising: at least a first adjustable strap which snugly engages about the head of a wearer about a front to back circumference of the head and at least a second adjustable strap extending downwardly and rearwardly from opposite positions along the first adjustable strap into a position where it abuts an area at the juncture of the head and an area the neck known as the suboccipital area, with at least the second adjustable strap being releasably inflatable to apply pressure against the suboccipital area, wherein the first adjustable strap is also releasably inflatable.

A headache mitigating apparatus comprising: at least a first adjustable strap which snugly engages about the head of a wearer about a front to back circumference of the head and at least a second adjustable strap extending downwardly and rearwardly from opposite positions along the first adjustable strap into a position where it abuts an area at the juncture of the head and an area the neck known as the suboccipital area, with at least the second adjustable strap being releasably inflatable to apply pressure against the suboccipital area, wherein the first adjustable strap is also releasably inflatable, wherein the straps further include cavities therein into which replaceable hot or cold inserts may be inserted to apply heat or cold as desired.

It should be noted that various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein.

What is claimed:

1. A headache mitigating apparatus comprising: at least a first adjustable strap which snugly engages about a front to back circumference of a head of a user and at least a second adjustable strap extending downwardly and rearwardly from opposite positions along the first adjustable strap into a position where it abuts an area known as the suboccipital area, with at least the second adjustable strap having an internal releasably inflatable bladder to apply pressure against the suboccipital area.

2. The headache mitigating apparatus of claim 1 wherein the first adjustable strap is also releasably inflatable.

3. The headache mitigating apparatus of claim 1 wherein the second adjustable strap further incorporates a forwardly and upwardly extending portion disposed on an opposite side of the first strap as compared to the portion of the second adjustable strap extending downwardly and rearwardly from opposite positions along the first adjustable strap.

4. The headache mitigating apparatus of claim 3 wherein the forwardly and upwardly extension is also provided with a releasably inflatable bladder.

5. The headache mitigating apparatus of claim 1 wherein the straps include bladders therein which may be inflated or deflated via use of a hand pump.

6. The headache mitigating apparatus of claim 1 wherein the straps include bladders therein which may be inflated or deflated via use of a mechanical pump carried by the apparatus.

7. The headache mitigating apparatus of claim 1 wherein the straps further include cavities therein into which replaceable hot or cold inserts may be inserted to apply heat or cold as desired.

8. The headache mitigating apparatus of claim 1 wherein the straps further include hot or cold inserts which are permanently affixed to the straps.

9. The headache mitigating apparatus of claim 1 further including a pressure control valve to limit inflation of the bladders.

10. The headache mitigating apparatus of claim 9 wherein the cavities may alternatively house protrusion inserts that apply localized pressure.

11. The headache mitigating apparatus of claim 9 wherein the cavities may alternatively house magnets.

12. The headache mitigating apparatus of claim 9 wherein the cavities may alternatively house aromatherapy inserts.

13. The head mitigating apparatus of claim 1 wherein all inflatable bladders are interconnected.

14. The head mitigating apparatus of claim 1, wherein the area of each bladder(s) and the force of air delivered by the pump into said bladder(s) may create a $P_h$ of at least 0.01 $lb_f/in^2$ in each bladder whereas $P_h=F_a/A_b$.

15. The head mitigating apparatus of claim 1, wherein the summative $P_h$ from the bladder(s) creates a $F_h$ greater than 0.1 kg·m/s² to the user's head/neck whereas $P_h$=Pressure in bladders, $F_h$=Force applied to the head, $F_a$=force applied by pump to an individual bladder, $A_b$=the area of an individual bladder and $P_h=F_a/A_b$.

16. A headache mitigating apparatus comprising:
at least a first adjustable strap which snugly engages about a front to back circumference of a head and at least a second adjustable strap extending downwardly and rearwardly from opposite positions along the first adjustable strap into a position where it abuts an area known as the suboccipital area, with at least the second adjustable strap having an internal releasably inflatable bladder to apply pressure against the suboccipital area; wherein the first adjustable strap also has an internal releasably inflatable bladder.

17. A headache mitigating apparatus comprising:
at least a first adjustable strap which snugly engages about a front to back circumference of a head and at least a second adjustable strap extending downwardly and rearwardly from opposite positions along the first adjustable strap into a position where it abuts an area known as the suboccipital area, with at least the second adjustable strap being internally releasably inflatable to apply pressure against the suboccipital area; wherein the first adjustable strap is also internally releasably inflatable, wherein the straps further include cavities therein into which replaceable hot or cold inserts may be inserted to apply heat or cold as desired.

\* \* \* \* \*